(12) United States Patent
Hosaka et al.

(10) Patent No.: US 8,758,230 B2
(45) Date of Patent: *Jun. 24, 2014

(54) ENDOSCOPE APPARATUS

(75) Inventors: Yoichi Hosaka, Iruma (JP); Yoshihisa Ishikawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/454,325

(22) Filed: Apr. 24, 2012

(65) Prior Publication Data

US 2012/0209065 A1 Aug. 16, 2012

Related U.S. Application Data

(63) Continuation of application No. PCT/JP2010/073377, filed on Dec. 24, 2010.

(51) Int. Cl.
*A61B 1/00* (2006.01)

(52) U.S. Cl.
CPC .................................. *A61B 1/00066* (2013.01)
USPC ............................................ 600/131; 348/75

(58) Field of Classification Search
USPC ........ 348/75, 76; 359/803; 396/17; 165/11.2; 600/103, 131, 146, 149, 104, 114; D24/137, 138
See application file for complete search history.

(56) References Cited

U.S. PATENT DOCUMENTS

| | | | |
|---|---|---|---|
| 4,742,819 A | 5/1988 | George | |
| 5,183,031 A | 2/1993 | Rossoff | |
| 5,373,317 A | 12/1994 | Salvati et al. | |
| D358,471 S | 5/1995 | Cope et al. | |
| 5,785,644 A | 7/1998 | Grabover et al. | |
| 6,315,712 B1 | 11/2001 | Rovegno | |
| 6,432,046 B1 | 8/2002 | Yarush et al. | |

(Continued)

FOREIGN PATENT DOCUMENTS

| | | |
|---|---|---|
| EP | 0 655 710 A2 | 5/1995 |
| FR | 2 740 688 A1 | 5/1997 |

(Continued)

OTHER PUBLICATIONS

International Search Report dated Feb. 1, 2011 in counterpart International Application No. PCT/JP2010/073377.
Japanese Office Action dated Sep. 20, 2011 (and English translation thereof) in counterpart Japanese Application No. 2011-527144.
Japanese Office Action dated Nov. 15, 2011 (and English translation thereof) in counterpart Japanese Application No. 2011-527144.
Japanese Notice of Allowance dated Dec. 13, 2011 (and English translation thereof) in counterpart Japanese Application No. 2011-527144.

(Continued)

*Primary Examiner* — Alireza Nia
*Assistant Examiner* — Timothy J Neal
(74) *Attorney, Agent, or Firm* — Holtz Holtz Goodman & Chick PC

(57) ABSTRACT

An endoscope apparatus includes an insertion part which has an imaging mechanism at a distal end portion; a display part which displays an image acquired by an observation mechanism, a manipulating part which performs curving manipulation of the insertion part; and a housing which accommodates the display part and the manipulating part to a front face thereof, and which connects the insertion part with a back face opposite to the front face. The manipulating part has a swingable first joystick; and a curving mechanism having the first joystick and a manipulating member connected thereto. The swinging center of the first joystick is located inside a region specified by a portion where fingers are arranged in a side view of the housing when a user holds the housing, and by a distal end of the first joystick protruding toward the front face.

8 Claims, 15 Drawing Sheets

(56) References Cited

U.S. PATENT DOCUMENTS

| | | | |
|---|---|---|---|
| 6,554,765 | B1 | 4/2003 | Yarush et al. |
| 6,636,254 | B1 | 10/2003 | Onishi et al. |
| 6,752,758 | B2 | 6/2004 | Motoki et al. |
| 7,074,182 | B2 | 7/2006 | Rovegno |
| D533,939 | S | 12/2006 | Root et al. |
| 7,179,223 | B2 | 2/2007 | Motoki et al. |
| D560,804 | S | 1/2008 | Pease et al. |
| D581,051 | S | 11/2008 | Melder |
| 7,679,041 | B2 | 3/2010 | Lia |
| 7,956,888 | B2 | 6/2011 | Karpen |
| 8,177,710 | B1 | 5/2012 | Hosaka et al. |
| 8,182,416 | B1 | 5/2012 | Hosaka et al. |
| 2004/0054254 | A1* | 3/2004 | Miyake .................. 600/104 |
| 2005/0119522 | A1 | 6/2005 | Okada |
| 2005/0256375 | A1* | 11/2005 | Freed .................... 600/146 |
| 2006/0281972 | A1 | 12/2006 | Pease et al. |
| 2007/0106117 | A1 | 5/2007 | Yokota |
| 2007/0156018 | A1 | 7/2007 | Krauter et al. |
| 2007/0188604 | A1 | 8/2007 | Miyamoto et al. |
| 2007/0249904 | A1 | 10/2007 | Amano et al. |
| 2007/0270647 | A1* | 11/2007 | Nahen et al. .......... 600/131 |
| 2008/0009677 | A1 | 1/2008 | Shoroji et al. |
| 2008/0052945 | A1 | 3/2008 | Matas et al. |
| 2009/0225159 | A1 | 9/2009 | Schneider et al. |
| 2009/0284649 | A1 | 11/2009 | Pease et al. |
| 2012/0209066 | A1 | 8/2012 | Hosaka et al. |
| 2012/0209067 | A1 | 8/2012 | Hosaka et al. |
| 2012/0209068 | A1 | 8/2012 | Hosaka et al. |

FOREIGN PATENT DOCUMENTS

| | | |
|---|---|---|
| JP | 52-143290 U | 10/1977 |
| JP | 59-5901 U | 1/1984 |
| JP | 62-8727 A | 1/1987 |
| JP | 4-090743 A | 3/1992 |
| JP | 6-217935 A | 8/1994 |
| JP | 2004-065832 A | 3/2004 |
| JP | 2004-109222 A | 4/2004 |
| JP | 2005-131161 A | 5/2005 |
| JP | 2005-224521 A | 8/2005 |
| JP | 2006-204582 A | 8/2006 |
| JP | 2009-189685 A | 8/2009 |
| WO | WO 97/15144 A1 | 4/1997 |
| WO | WO 2007/002526 A1 | 1/2007 |

OTHER PUBLICATIONS

U.S. Appl. No. 13/196,468; First Named Inventor: Yoichi Hosaka; Title: "Endoscopic Device", filed Aug. 2, 2011.
U.S. Appl. No. 13/196,373; First Named Inventor: Yoichi Hosaka; Title: "Endoscopic Device", filed Aug. 2, 2011.
U.S. Appl. No. 13/454,364; First Named Inventor: Yoichi Hosaka; Title: "Endoscope Apparatus", filed Apr. 24, 2012.
U.S. Appl. No. 13/454,423; First Named Inventor: Yoichi Hosaka; Title: "Endoscope Apparatus", filed Apr. 24, 2012.
U.S. Appl. No. 13/454,500; First Named Inventor: Yoichi Hosaka; Title: "Endoscope Apparatus", filed Apr. 24, 2012.
Extended European Search Report (EESR) dated Sep. 19, 2012 (in English) issued in counterpart European Application No. 10858786.6.
International Search Report (ISR) dated Feb. 1, 2011 (in English) issued in International Application No. PCT/JP2010/073377, which is the parent International application of the present application.
International Search Report (ISR) dated Feb. 1, 2011 (in English) issued in International Application No. PCT/JP2010/073439, which is the parent International application of related U.S. Appl. No. 13/454,364.
Japanese Office Action dated Sep. 20, 2011 (and English translation thereof) issued in Japanese Application No. 2011-527534, which is a counterpart Japanese application of related U.S. Appl. No. 13/454,364.
Japanese Office Action dated Nov. 15, 2011 (and English translation thereof) issued in Japanese Application No. 2011-527534, which is a counterpart Japanese application of related U.S. Appl. No. 13/454,364.
Japanese Notice of Allowance dated Dec. 13, 2011 (and English translation thereof) issued in Japanese Application No. 2011-527534, which is a counterpart Japanese application of related U.S. Appl. No. 13/454,364.
Extended European Search Report (EESR) dated Oct. 15, 2012 (in English) issued in European Application No. 10858783.3, which is a counterpart European application of related U.S. Appl. No. 13/454,364.
International Search Report (ISR) dated Feb. 1, 2011 (in English) issued in International Application No. PCT/JP2010/073281, which is the parent International application of related U.S. Appl. No. 13/454,423.
Japanese Office Action dated Sep. 20, 2011 (and English translation thereof) issued in Japanese Application No. 2011-527103, which is a counterpart Japanese application of related U.S. Appl. No. 13/454,423.
Japanese Office Action dated Nov. 15, 2011 (and English translation thereof) issued in Japanese Application No. 2011-527103, which is a counterpart Japanese application of related U.S. Appl. No. 13/454,423.
Japanese Notice of Allowance dated Dec. 13, 2011 (and English translation thereof) issued in Japanese Application No. 2011-527103, which is a counterpart Japanese application of related U.S. Appl. No. 13/454,423.
Extended European Search Report (EESR) dated Aug. 27, 2012 (in English) issued in European Application No. 10858785.8, which is a counterpart European application of related U.S. Appl. No. 13/454,423.
International Search Report (ISR) dated Feb. 1, 2011 (in English) issued in International Application No. PCT/JP2010/073378, which is the parent International application of related U.S. Appl. No. 13/454,500.
Japanese Office Action dated Sep. 20, 2011 (and English translation thereof) issued in Japanese Application No. 2011-528110, which is a counterpart Japanese application of related U.S. Appl. No. 13/454,500.
Japanese Office Action dated Nov. 15, 2011 (and English translation thereof) issued in Japanese Application No. 2011-528110, which is a counterpart Japanese application of related U.S. Appl. No. 13/454,500.
Japanese Notice of Allowance dated Dec. 13, 2011 (and English translation thereof) issued in Japanese Application No. 2011-528110, which is a counterpart Japanese application of related U.S. Appl. No. 13/454,500.
U.S. Notice of Allowance dated Jan. 17, 2012 issued in related U.S. Appl. No. 13/196,468.
U.S. Notice of Allowance dated Jan. 23, 2012 issued in related U.S. Appl. No. 13/196,373.
U.S. Office Action dated May 24, 2013 issued in related U.S. Appl. No. 13/454,364.
U.S. Office Action dated Jun. 19, 2013 issued in related U.S. Appl. No. 13/454,423.
U.S. Office Action dated Jun. 28, 2013 issued in related U.S. Appl. No. 13/454,500.
Final Office Action dated Oct. 4, 2013 issued in related U.S. Appl. No. 13/454,364.
Final Office Action dated Oct. 4, 2013 issued in related U.S. Appl. No. 13/454,423.
Final Office Action dated Oct. 10, 2013 issued in related U.S. Appl. No. 13/454,500.
U.S. Office Action dated Feb. 26, 2014 issued in related U.S. Appl. No. 13/454,423.
U.S. Office Action dated Feb. 26, 2014 issued in related U.S. Appl. No. 13/454,500.

* cited by examiner

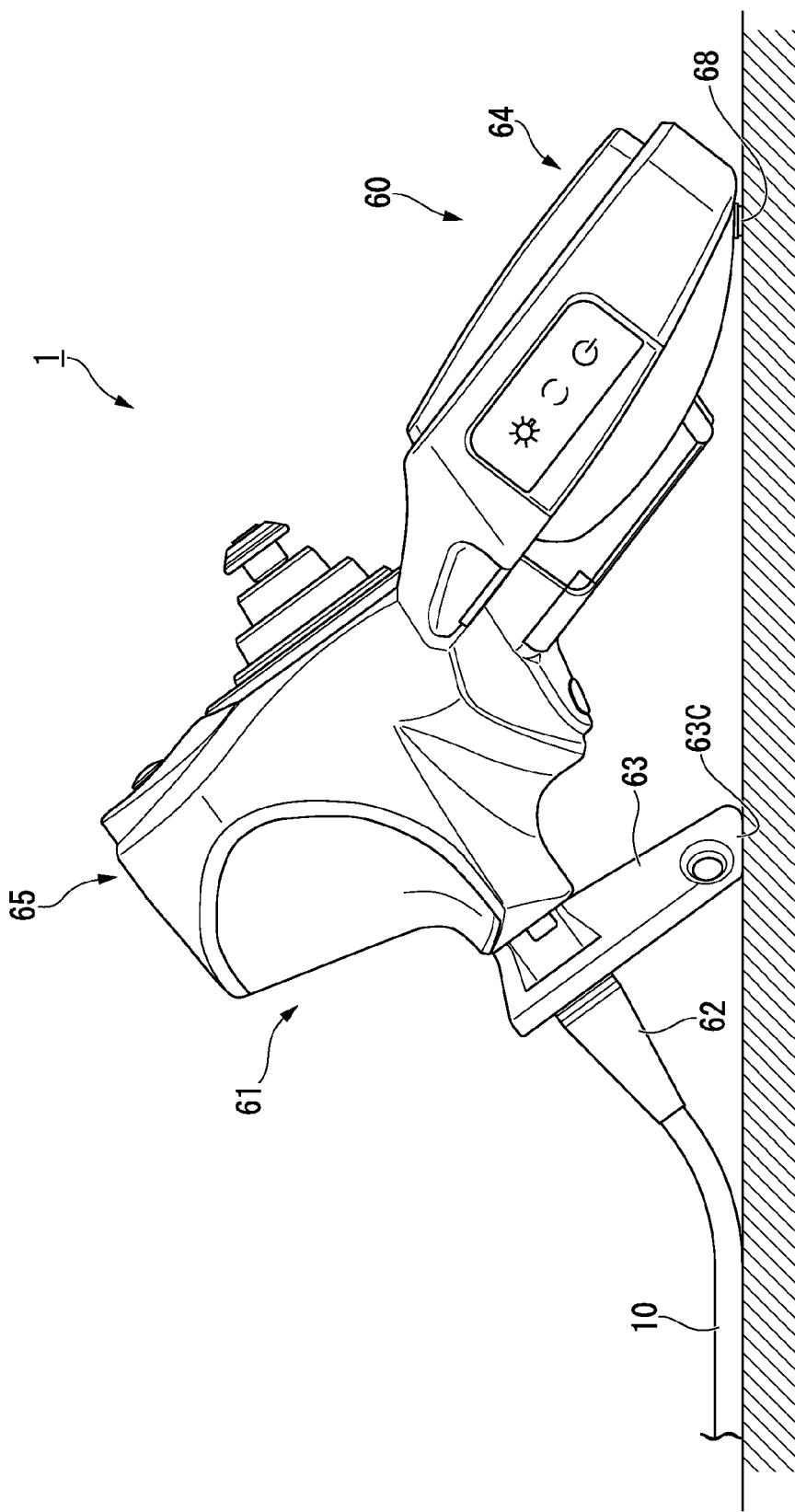

ENDOSCOPE APPARATUS

This application is a continuation application based on a PCT Patent Application No. PCT/JP2010/073377, filed on Dec. 24, 2010. The content of the PCT Application is incorporated herein by reference.

BACKGROUND OF THE INVENTION

1. Field of the Invention

The present invention relates to an endoscope apparatus, and more particularly, to an endoscope apparatus in which a manipulating part that curves an insertion part and a display part that displays an image acquired by the insertion part are accommodated in the same housing.

2. Description of the Related Art

An endoscope apparatus including an imaging mechanism at a distal end portion of a long insertion part is widely used for observation of a specimen beyond an elongated insertion path, internal observation of a specimen, or the like.

In recent years, as one direction for improvement of endoscope apparatuses, it has being studied in which a display part that displays an image acquired by an insertion part and a manipulating part that performs curving manipulation of the insertion part are accommodated in one housing, and in which carrying and manipulation of an endoscope apparatus are made easy.

Japanese Unexamined Patent Application, First Publication No. 2004-109222 discloses an endoscope apparatus in which a display part and a manipulating part are accommodated in a common housing. In this endoscope apparatus, a monitor part is arranged at one end of the housing, and a substantially rod-shaped grip is formed at the other end. The manipulating part having a joystick is arranged between a grip and a monitor part, and when a user manipulates the joystick, the joystick is manipulated by the thumb with the rod-shaped grip grasped.

SUMMARY OF THE INVENTION

An endoscope apparatus according to a first aspect of the present invention includes an insertion part which has an imaging mechanism at a distal end portion and which is bendable and elongated; a display part which displays an image acquired by the imaging mechanism; a manipulating part which performs curving manipulation of the insertion part; and a housing being provided with the display part and the manipulating part to a front face thereof, and being connected with the insertion part with a back face opposite to the front face. The manipulating part has a swingable manipulating rod; and a curving mechanism that has the manipulating rod and the manipulating member connected thereto and that curves the insertion part as the manipulating member is advanced or retracted by manipulating the manipulating rod. The housing has an upper portion to which the display part is provided therewith, and a lower portion where the manipulating part provided therewith and having the insertion part connected thereto. A proximal end of the insertion part connected to the lower portion, and the manipulating rod are coaxially arranged in a neutral state of the manipulating rod. The housing is held such that the thumb of one hand of a user is located at a distal end of the manipulating rod, the other fingers in the one hand of the user are located above and below the proximal end of the insertion part in the back face, and the thumb and the other fingers face each other. The swinging center of the manipulating rod is located inside a region specified by the portion of the back face where the other fingers are arranged in a side view of the housing when the user holds the housing, and by the distal end of the manipulating rod protruding toward the front face.

In an endoscope apparatus according to a second aspect of the present invention, the back face has a first slope and a second slope that rise up toward the connected insertion part, and when the user holds the housing in order to use the endoscope apparatus, at least one of the other finger may be arranged at each of the first slope and the second slope.

In an endoscope apparatus according to a third aspect of the present invention, the curving mechanism is a mechanical curving mechanism in which the manipulating member is advanced or retracted by manipulating the manipulating rod.

BRIEF DESCRIPTION OF THE DRAWINGS

FIG. 8 is a view showing a ground contact aspect in an inverted mode of the endoscope apparatus.

DESCRIPTION OF EMBODIMENTS

Figure 1:
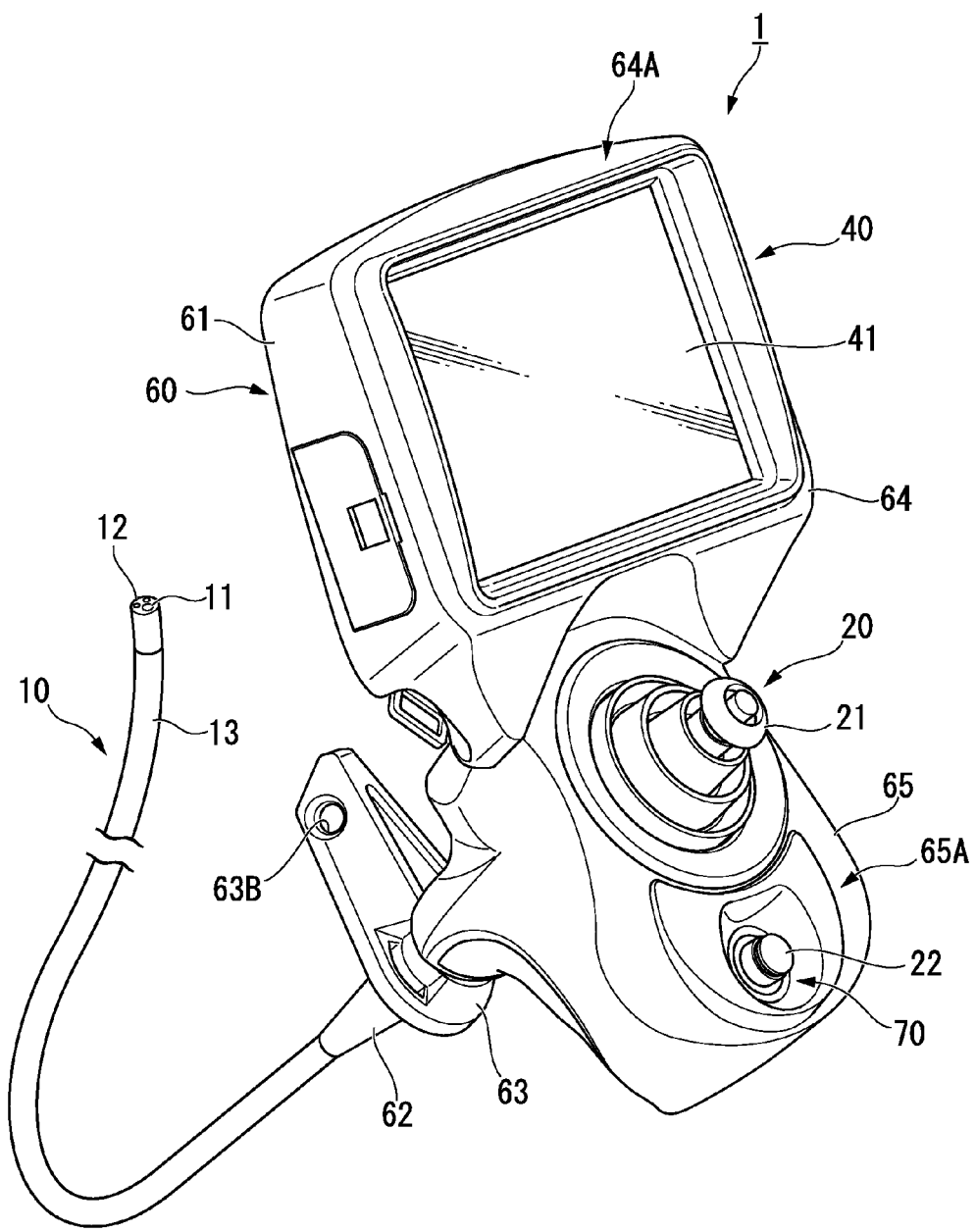
FIG. 1 is an overall perspective view showing an endoscope apparatus of one embodiment of the present invention.

An endoscope apparatus of one embodiment of the present invention will be described with reference to FIGS. 1 to 11. An endoscope apparatus 1 of the present embodiment is used for observation of a specimen at the point of an elongated insertion path, internal observation of a specimen, or the like. As shown in FIG. 1, the endoscope apparatus 1 includes a long insertion part 10, a manipulating part 20 for performing curving manipulation of the insertion part 10, a display part 40 that displays an image acquired by the insertion part 10, and a housing part 60 including a housing 61 that accommodates the manipulating part 20 and the display part 40.

The insertion part 10 has a well-known configuration in which a distal end portion thereof includes an illumination mechanism 12, such as an observation optical system 11 and an LED, and an imaging mechanism 56, such as a CCD (not shown), and can acquire an image, such as a still image, a moving image, or the like of a specimen in front of the distal end portion. Additionally, the insertion part 10 has a well-known curving portion 13 in which a plurality of joint rings or curvable pieces (hereinafter generically referred to as "joint rings or the like") that is not shown is arranged and coupled together in the direction of an axis. The insertion part 10 can be curved in four directions apart from the center axis in two axes that intersect its own center axis. Manipulating members, such as four wires that corresponds to the four directions, are connected to a joint ring or the like at the most distal end among the plurality of joint rings or the like. Each manipulating member extends to the inside of the housing part 60 through each joint ring or the like, and is connected to the manipulating part 20.

The manipulating part 20 has a first joystick (manipulating rod) 21 for manipulating the curving portion 13, a second joystick 22 for manipulating a cursor or the like displayed on the display part 40, and a curving mechanism manipulated via the first joystick 21.

Figure 2:
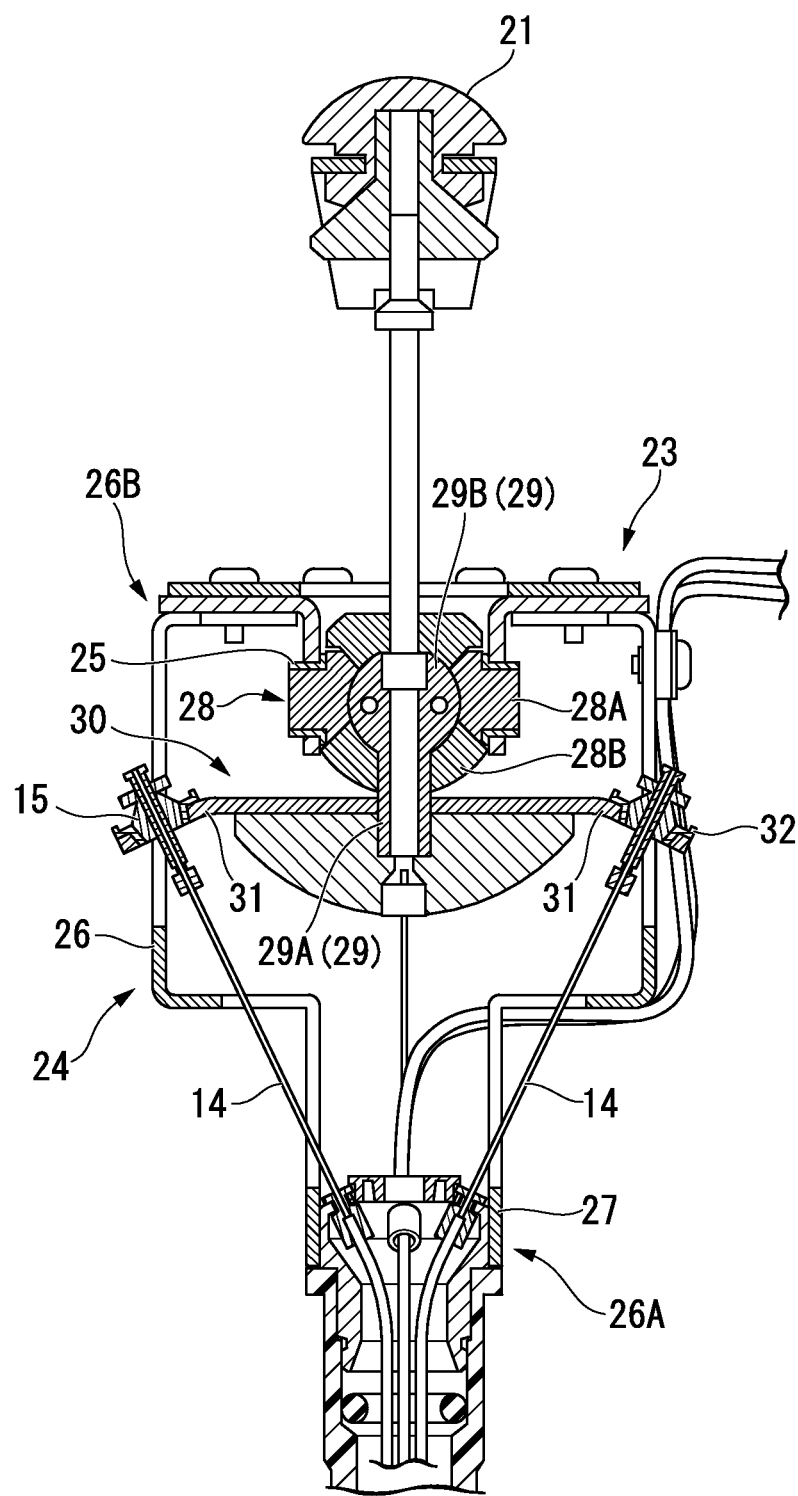
FIG. 2 is a diagram showing a first joystick and a manipulating mechanism of the endoscope apparatus.

FIG. 2 is a diagram showing the first joystick 21 and the curving mechanism 23.

The curving mechanism 23 includes a frame body 24, and a swinging body 25 attached to the frame body 24. The frame body 24 is formed of a material having a certain rigidity, such as metal, and includes a swinging body accommodation portion 26 to which the swinging body is attached, and a guide portion 27 provided to extend from the swinging body accommodation portion 26.

The swinging body 25 includes a first member 28 rotatably attached to the frame body 24, a second member 29 rotatably attached to the first member 28, and a manipulating member fixing portion 30 attached to the second member 29.

The first member 28 is formed of metal, resin, or the like, and has a rotating shaft portion 28A. The swinging body accommodation portion includes the first end 26A to which the guide portion 27 extends, and the second end 26B which is opposite to the first end 26A. The first member 28 is attached to the second end 26B of the swinging body accommodation portions 26 so as to be able to rotate on the axis of the rotating shaft portion 28A by a predetermined range.

The second member 29 is formed of metal, resin, or the like, and has a substantially columnar shaft portion 29A and a rotating shaft portion 29B that is formed substantially in the shape of a column and is formed at one end of the shaft portion 29A. The center axis of the shaft portion 29A and the center axis of the rotating shaft portion 29B are orthogonal to each other. The second member 29 is attached to the first member 28 so that both of the axis of the shaft portion 29A and the axis of the rotating shaft portion 29B are orthogonal to the center axis of the rotating shaft portion 28A of the first member 28. The second member 29 can be rotated about the axis of the rotating shaft portion 29B with respect to the first member 28 in a predetermined range by a cutout portion 28B which is formed in the first member 28 so as not to interfere with the shaft portion 29A.

The manipulating member fixing portion 30 includes a first arm portion 31 that protrudes toward both sides in a first direction, and a second arm portion (not shown) that protrudes toward both sides in a second direction which is orthogonal to the first arm portion. Ends of the four manipulating members 14 extending from the insertion part 10 are fixed to both longitudinal ends of the first arm portion 31 and the second arm portion. A connecting member 15 is attached to the end of each manipulating member 14. Both the longitudinal ends of the first arm portion 31 and the second arm portion are provided with receiving members 32 to which the connecting member 15 is attached, and each manipulating member 14 is connected and fixed to the manipulating member fixing portion 30 by inserting each connecting member 15 into each receiving member 32.

As shown in FIG. 2, the swinging body 25 is attached to the second end 26B of the swinging body accommodation portion 26 so that the center axis of the shaft portion 29A of the second member 29 becomes substantially coaxial with the center axis of the guide portion 27 of the frame body 24. The four manipulating members 14 extending from the insertion part 10 are connected to the manipulating member fixing portion 30 through the guide portion 27. The shape of the frame body 24 is set so as not to interfere with the swinging of the swinging body 25, and the push or pull (advance or retreat) of the manipulating member 14 accompanying this.

The first joystick 21 is attached to the second member 29 so as to become substantially coaxial with the shaft portion 29A of the second member 29. Accordingly, the first joystick 21 is inclined in arbitrary directions, so that the swinging body 25 can be swung with respect to the frame body 24 and the manipulating member 14 connected to the manipulating member fixing portion 30 can be advanced or retracted in the longitudinal direction of the insertion part 10. As a result, the curving portion 13 can be curved in a direction opposite to the direction in which the first joystick 21 is inclined.

The second joystick 22 is an electrical manipulating mechanism of which one end is attached to a substrate. The inclined direction of the second joystick 22 is inputted to the substrate there by, a cursor is moved in the direction.

As shown in FIG. 1, the display part 40 has a well-known configuration including a display 41, such as an LCD, and a control substrate (to be described below) that controls display of the display 41. An aspect in which the display part 40 is accommodated in the housing 61 will be described in detail in the description of the housing part 60.

The housing part 60 includes a housing 61 in which the manipulating part 20 and the display part 40 are accommodated, a reinforcing member 62 attached to a connecting portion between the housing 61 and the insertion part 10, and a holder (self-supporting auxiliary member) 63 attached to the proximal end of the insertion part 10.

The housing 61 is formed of resin or the like, and includes an upper portion 64 provided with the display part 40, and a lower portion 65 connected to the upper portion 64 and having the manipulating part 20 arranged therein.

Figure 3:
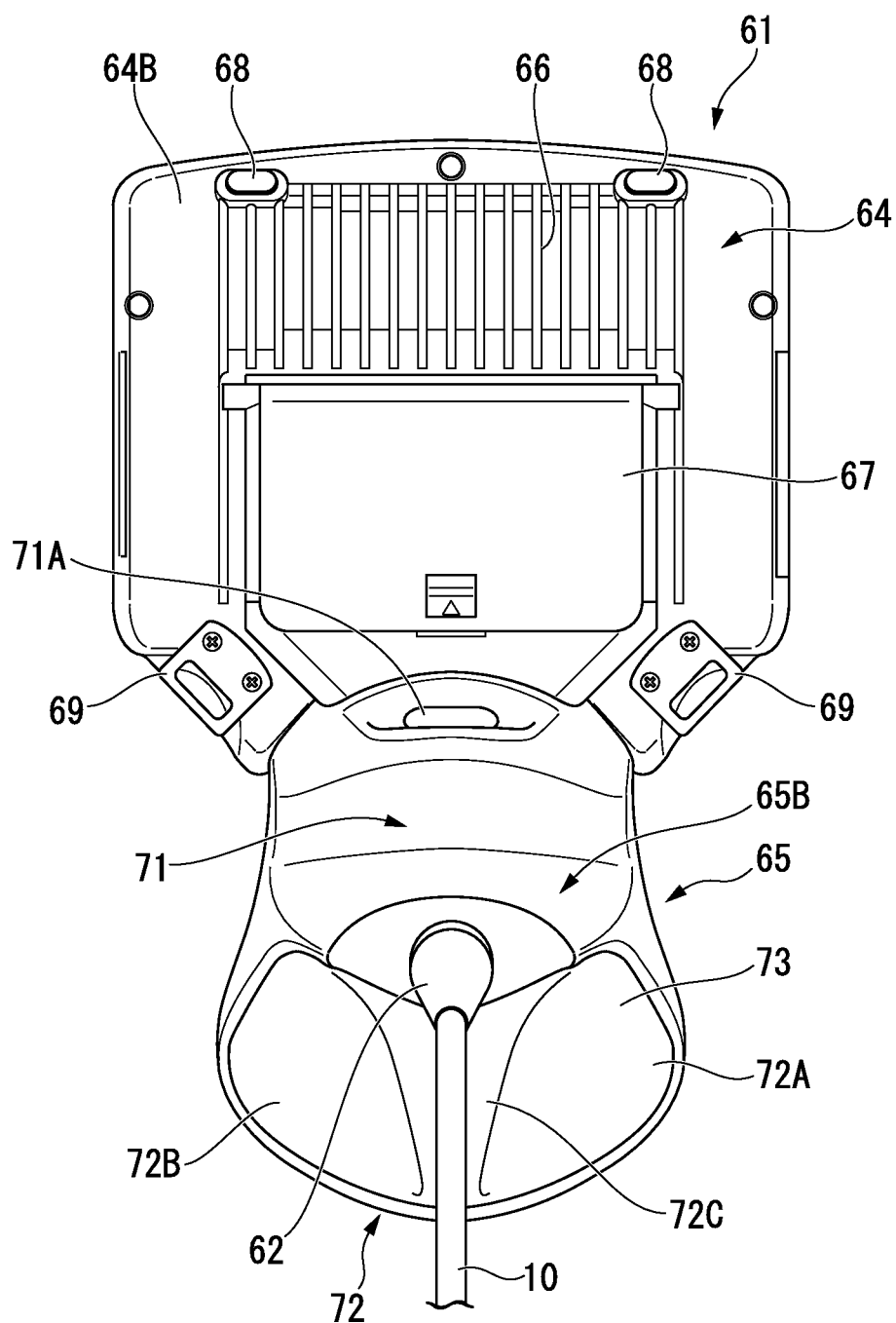
FIG. 3 is a back view of a housing of the endoscope apparatus.

FIG. 3 is a back view of the housing 61 that is shown with the holder 63 shown in FIG. 1 is omitted. As shown in FIGS. 1 and 3, the upper portion 64 is formed in a substantially rectangular parallelepiped shape corresponding to the display 41 of the display part 40, and the display 41 is arranged at a front face 64A. Within the back face 64B of the upper portion 64, fins 66 for heat dissipation are provided on the upper side of a back face 64B, and a lid 67 of a battery accommodation portion (to be described below) is provided on the lower side of the back face 64B. Furthermore, ground contact members 68 made from rubber, elastomer, or the like are attached to two locations of a top side edge of the back face 64B so as to enhance the frictional coefficient. Moreover, fittings 69 for attaching accessories, such as a strap, are attached to the lower side to which the lower portion 65 is connected.

Figure 4:
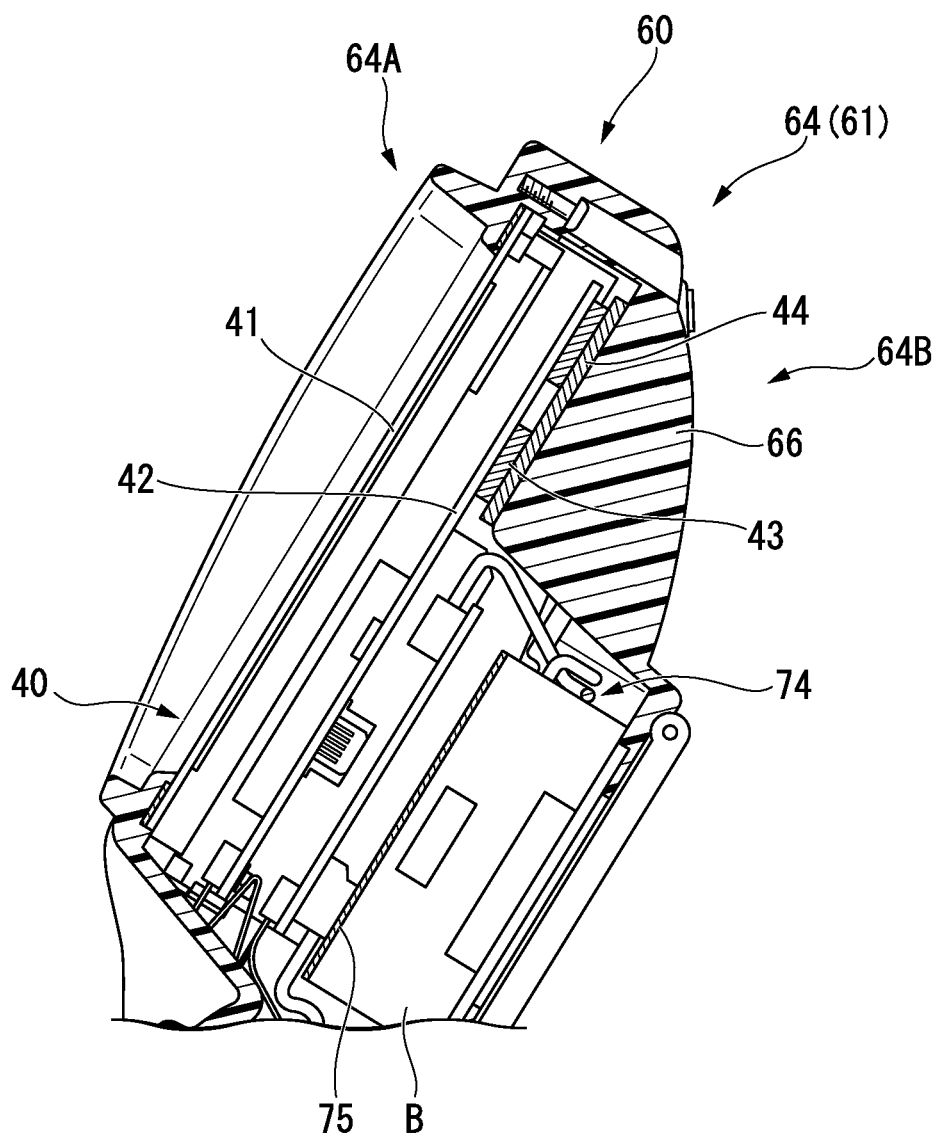
FIG. 4 is a cross-sectional view in an upper portion of the housing in a front-and-rear direction.
Figure 5:
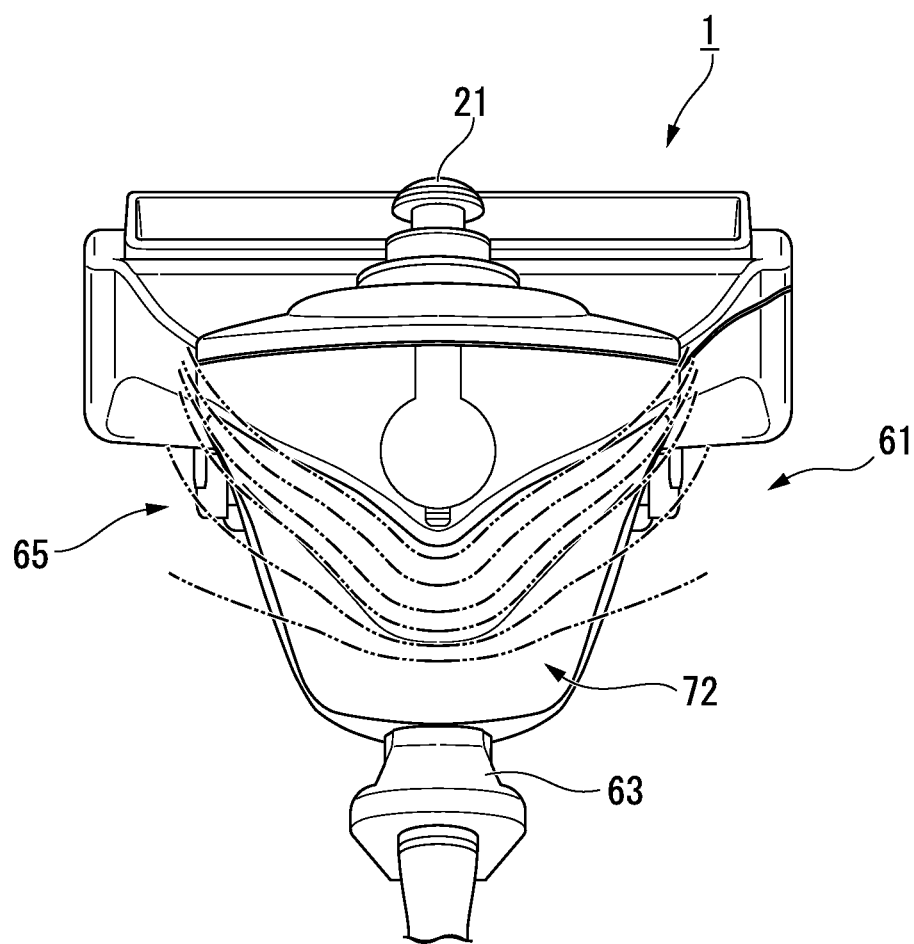
FIG. 5 is a bottom plan view of the housing.

FIG. 4 is a cross-sectional view of the upper portion 64 in the front-and-rear direction. Within the upper portion 64, the display part 40 is accommodated at the front face 64A, and the battery B is arranged at the back face 64B. A control board 42 having an IC 43 is connected to the display 41. The control board 42 is accommodated on the back side of the display 41 in a state that the IC 43 is faced the back face 64B.

The IC 43 that emits heat during operation is accommodated at a position near the fins 66 provided at an upper portion of the back face 64B, and a heat-conduction sheet 44 is interposed between the IC 43 and the fins 66.

The battery B is accommodated in the battery accommodation portion 74 formed closer to the back face than the control board 42. A heat insulation sheet 75 is arranged at a wall surface on the front side of the battery accommodation portion 74 so that the heat emitted from the battery B is not easily transferred to the display part 40.

Through the above configuration, the IC 43 and the battery B that generate heat when the endoscope apparatus 1 is used are arranged apart from each other. Generation of heat from the IC 43 is efficiently diffused to the outside of the apparatus from the fins 66 through the heat-conduction sheet 44, and generation of heat of the battery B is not easily transferred to the display part 40 as described above. As a result, a structure in which display of the display 41 or the like is not affected while accommodating two heating elements of the IC 43 and the battery B in the upper portion 64 is realized.

The lower portion 65 is a portion that a user holds with a hand when the endoscope apparatus 1 is used and manipulated. As shown in FIG. 1, the lower portion 65 is connected to the upper portion 64 with an upper front face 64A, and a front face 65A of the lower portion 65 form a predetermined angle so that the display 41 is easily seen when a user holds the lower portion.

The peripheral edge of the front face 65A is formed by a curve, and has such a shape that is constricted and is narrowed at an intermediate portion in a vertical direction and becomes gradually wider toward the lower portion. Furthermore, the peripheral edge of the front face has a symmetrical shape so that the peripheral edge can be suitably held by a right or left hands.

The second joystick 22 of the two joysticks of the manipulating part 20 is arranged on the lower side of the front face 65A, and the first joystick 21 is arranged above the second joystick 22. A straight line that connects the first joystick 21 and the second joystick 22 together are on line where a central portion of the display part 40 in the right-and-left direction (direction orthogonal to the vertical direction of the housing 61), in the plan view of the housing 61. A distal end of the first joystick 21 protrudes above the front face 65A in a predetermined length so as to be easily manipulated by a user holding the lower portion 65. The second joystick 22 protrudes from the bottom of the concave portion 70 provided in the front face 65A. The second joystick 22 is set to have a height that the distal end thereof does not protrude from the front face 65A.

As shown in FIG. 3, the insertion part 10 is connected to a back face 65B of the lower portion 65. The insertion part 10 extends from an intermediate portion of the back face 65B in the vertical direction. A first slope 71 that rises up toward the insertion part 10 is formed on the side of the back face 65B above the insertion part 10. A second slope 72 that rises up toward the insertion part 10 is formed below the insertion part 10. The back face 65B of the lower portion 65 is formed in a shape, which becomes convex toward the back side in a side view of the housing 61, by the first slope 71 and the second slope 72. Through such a configuration, the back face 65B of the back face of the housing 61 is used as a portion (grip face) on which user's fingers are arranged when a user holds the housing 61.

The first slope 71 is set to have a dimension such that the index finger and middle finger of a hand with a standard size can be aligned in the vertical direction and can be hooked simultaneously, and functions as a first finger hook portion. The first slope 71 is provided with a freezing/recording button 71A for recording an image acquired by an imaging means of the insertion part 10 as a still image or a moving image, and the button can be manipulated by an index finger when a user holds the lower portion 65.

The second slope 72 is set to have a dimension such that the third finger and little finger of a hand with a standard size can be aligned in the vertical direction and can be hooked simultaneously. The second slope 72 functions as a second finger hook portion. As shown by a two-dot chain line shown in FIG. 5, the lower portion 65 is formed so that the cross-sectional area that is parallel to the right-and-left direction of the housing 61 and orthogonal to the vertical direction becomes gradually smaller toward the lower end by providing the second slope 72. The second slope 72 has a first holding face 72A and a second holding face 72B that incline toward the peripheral edges of the back face 65B in the right-and-left direction respectively. Additionally, the second slope 72 has a third holding face 72C that extends toward a lower peripheral edge of the back face 65B and connects the first holding face 72A to the second holding face 72B. Thereby, the second slope 72 is formed in a shape which becomes convex toward the back face 65B in a bottom view of the housing 61. A friction member 73 made of an elastically deformable material, such as rubber or elastomer, is attached to each face of the second slope 72. This makes the frictional coefficient of each holding face higher than other portions of the housing 61.

The reinforcing member 62 is formed substantially in the shape of a cylinder of which the external diameter of one end is reduced in the shape of a taper. The reinforcing member 62 is arranged so as to cover the proximal end of the insertion part 10 connected to the housing 61 and its surroundings. The reinforcing member 62 has certain rigidity and the portion of the insertion part 10 which is covered with the reinforcing member 62 maintains a linear state. That is, the reinforcing member 62 functions as a bending stopper that prevents the covered insertion part 10 from bending at a steep angle.

Figure 6:
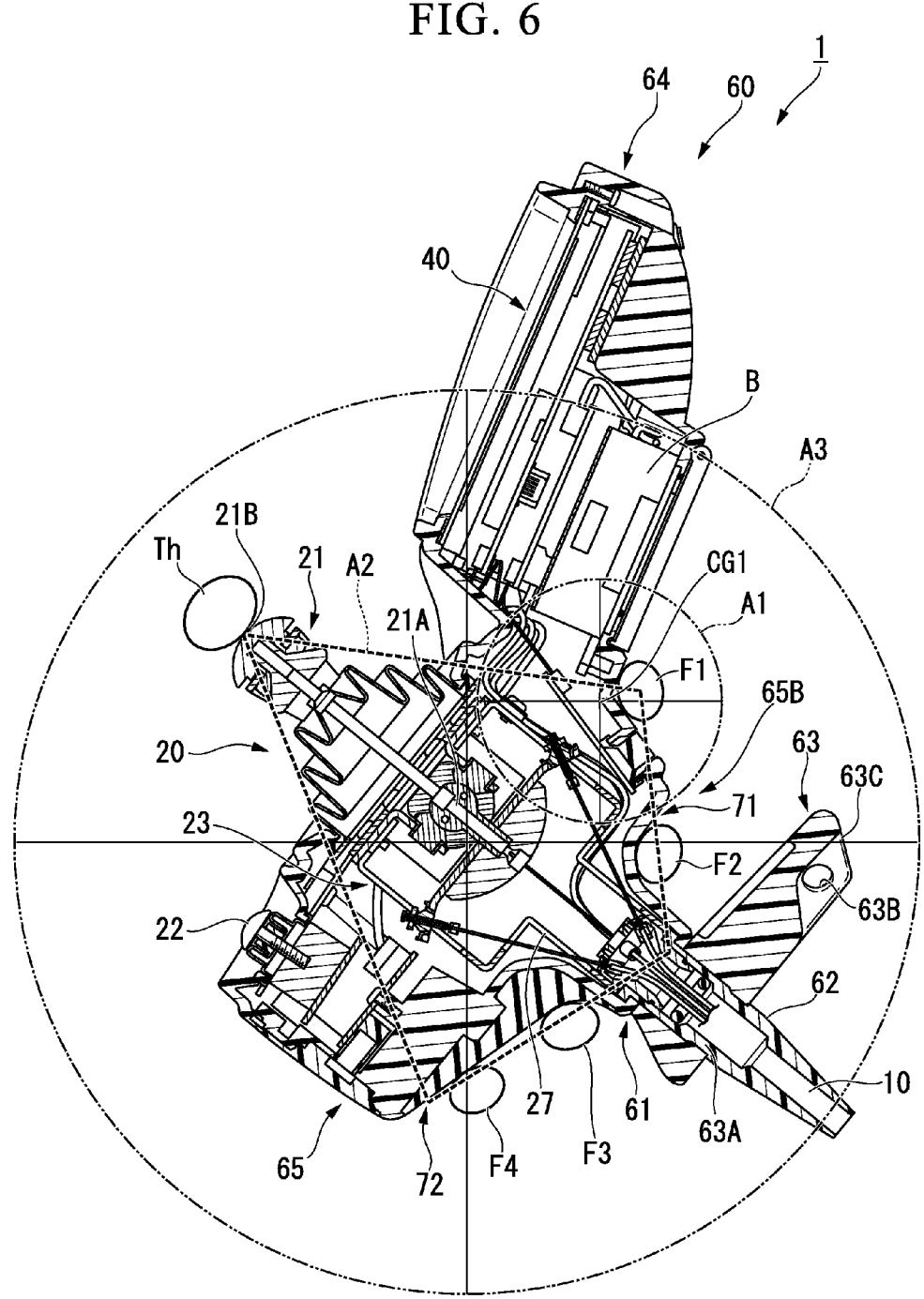
FIG. 6 is a cross-sectional view of a manipulating part, a display part, and a housing part of the endoscope apparatus along the center axis of an insertion part.

FIG. 6 is a cross-sectional view of the manipulating part 20, the display part 40, and the housing part 60 along the center axis of the insertion part 10. The holder 63 is formed of resin or the like, and as shown in FIG. 6, has a first through hole 63A with a larger diameter at a first end and has a second through hole 63B with a smaller diameter at a second end. The holder 63 is mounted on the connecting portion between the insertion part 10 and the housing 61 so that the reinforcing member 62 is inserted into the first through hole 63A. The internal diameter of the second through hole 63B is slightly larger than the external diameter of the insertion part 10 so that the through hole allows the insertion part 10 to be inserted thereinto and held thereby. The second end of the holder 63 is provided with a ground contact face 63C, and the details thereof will be described below.

As shown in FIG. 6, the curving mechanism 23 is accommodated in the lower portion 65 of the housing 61 so that the guide portion 27 is located at the back face 65B, and the center axis of the insertion part 10 and the first joystick 21 in a non-manipulated neutral state are made coaxial or substantially coaxial with each other.

Since the battery B is accommodated in the upper portion 64 of the housing 61, the center of gravity of the endoscope apparatus 1 excluding the insertion part 10 is set to a designed center-of-gravity position CG1 shown in FIG. 6 when the battery B is mounted and used. Although the actual center-of-gravity position moves slightly due to the allowable range for manufacturing errors or the like in an individual product, the position is present within a region within a predetermined radius having the designed center-of-gravity position CG1 as a center that is a region A1 substantially including the connecting portion between the upper portion 64 and the lower portion 65.

Figure 7:
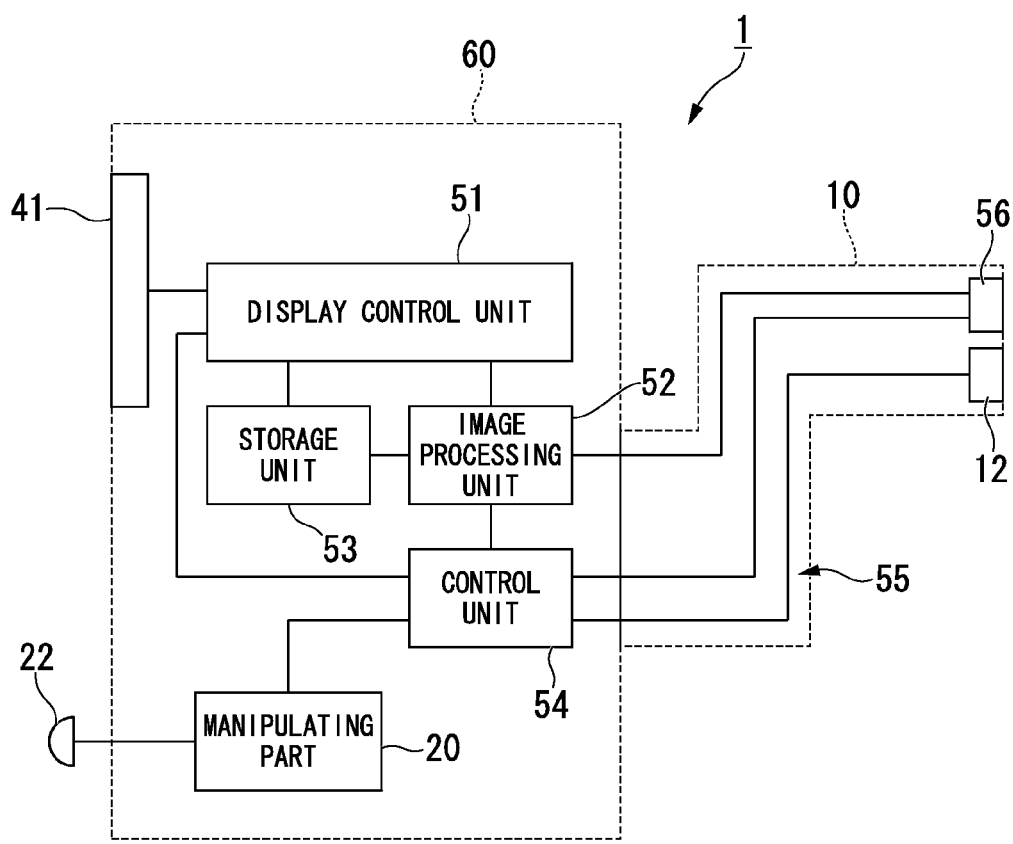
FIG. 7 is a functional block diagram of the endoscope apparatus.

FIG. 7 is a functional block diagram of the endoscope apparatus 1. In addition to the above-described display control unit 51, the endoscope apparatus 1 includes an image processing unit 52 that processes a video signal acquired by the imaging mechanism 56 of the insertion part 10, a storage unit 53 that stores the acquired still image, moving image, or the like, and a control unit 54 that controls the overall operation of the endoscope apparatus 1 including light quantity adjustment or the like of the illumination mechanism 12.

The image processing unit 52 and the control unit 54 are stored in, for example, an IC (not shown) that is attached to the control board 42. Various well-known storage media can be used as the storage unit 53, and the storage unit may be detachably attached to the housing part 60. The imaging mechanism 56 and the illumination mechanism 12 are connected to the image processing unit 52 or the control unit 54 by a wiring line 55 that extends to the inside of the housing part 60 through the insertion part 10. The second joystick 22 of the manipulating part 20 is electrically connected to the control unit 54 via the substrate (not shown).

The operation when the endoscope apparatus 1 configured as described above is used will be described.

With the battery B accommodated in and mounted on the battery accommodation portion 74, a user starts the endoscope apparatus 1, inserts the distal end of the insertion part 10 into the inside of a specimen, into an access path to the specimen, or the like, and advances the distal end to a part to be observed.

When the user wants to change the orientation of the distal end of the insertion part 10, the insertion part 10 can be curved in a desired orientation by manipulating the first joystick 21 of the manipulating part 20 to advance or retract the manipulating member 14 connected to the curving mechanism 23.

At this time, the user holds the lower portion 65 of the housing 61 so as to wrap around the lower portion with a dominant hand, and places and manipulates a thumb at the end of the first joystick 21 protruding from the front face 65A. An example of the positional relationship between user's fingers and the housing part 60 during the manipulation is shown in FIG. 6. During the manipulation, in a side view of the housing 61, at least the index finger F1 is located on the first slope 71 of the lower back face 65B, and the little finger F4 is located on the second slope 72. Accordingly, the connecting portion between the insertion part 10 and the housing part 60 is located between the index finger F1 and the little finger F4, and the insertion part 10 extends from the back face 65B that is a grip face.

In the example of FIG. 6, the middle finger F2 is arranged on the first slope 71 in addition to the index finger F1, and the third finger F3 is arranged on the second slope 72 in addition to the little finger F4.

When the distal end of the insertion part 10 reaches a part to be observed, the user performs observation or inspection of the specimen while manipulating the manipulating part 20. If needed, the freezing/recording button 71A is manipulated to record a still image, a moving image, or the like of a target part. Various acquired images are stored in the storage unit 53.

When a hand holding the housing 61 gets tired because the operating time becomes long, the housing 61 can be placed on the ground or on a desk and manipulated. When the housing 61 is placed, as shown in FIG. 8, the two ground contact members 68 provided at the upper portion 64, and the connecting portion between the insertion part 10 and the housing 61, more specifically, the connecting portion is a boundary portion between the reinforcing member 62 and the insertion part 10 including a predetermined range in front of or behind the boundary portion are brought into contact with the ground. Thereby, the housing 61 is suitably self-supported such that the upper portion 64 is turned down and the lower portion 65 is turned up.

Since the proximal end portion of the insertion part 10 extending from the housing 61 is held in the shape of a straight line by the reinforcing member 62, the proximal end is suitably self-supported without holder 63. However, as shown in FIG. 8, if the second end of the holder 63 is turned toward the upper portion 64 of the housing 61, the ground contact face 63C is located on the ground contact face of the housing 61 specified by the connecting portion that contacts the ground and the ground contact member 68. As a result, the holder 63 can assist the housing 61 in being suitably self-supporting, and can place the housing 61 in a more stable state. Hereinafter, the state in which the endoscope apparatus 1 is used with the housing 61 placed in this way is referred to as an "inverted mode".

When the apparatus is used with the housing 61 placed as described above, the user performs a predetermined manipulation input via the manipulating part 20 to switch a display mode of a screen. The display control unit 51 receives an input, and switches the display of the display 41 from a standard mode shown in FIG. 9A to the inverted mode shown in FIG. 9B.

Figure 9A:
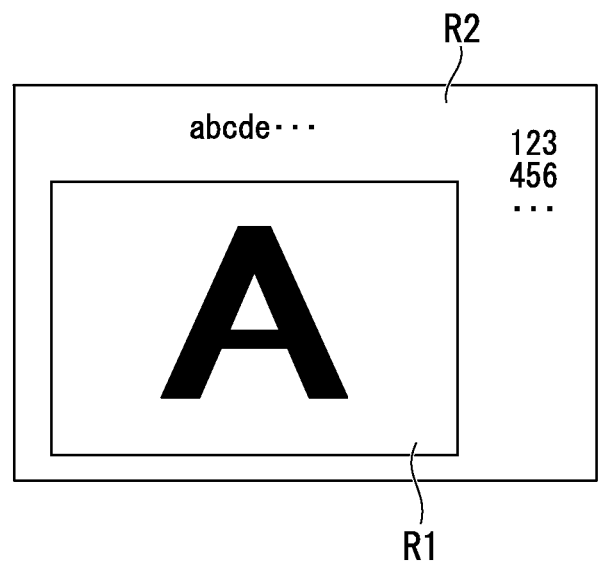
FIG. 9A is a view showing an example of screen display in a standard mode of the endoscope apparatus.
Figure 9B:
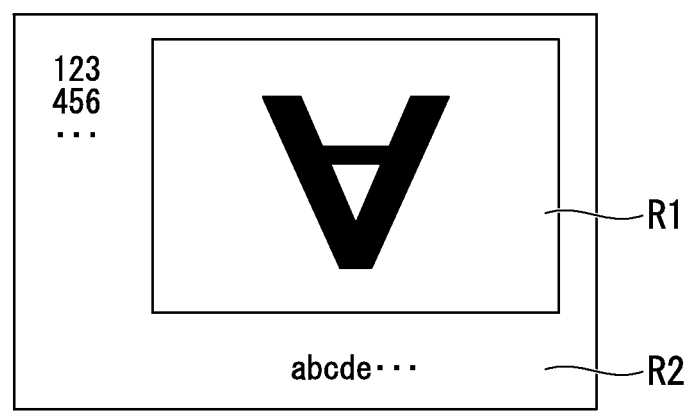
FIG. 9B is a view showing an example of screen display in the inverted mode of the endoscope apparatus.
Figure 10A:
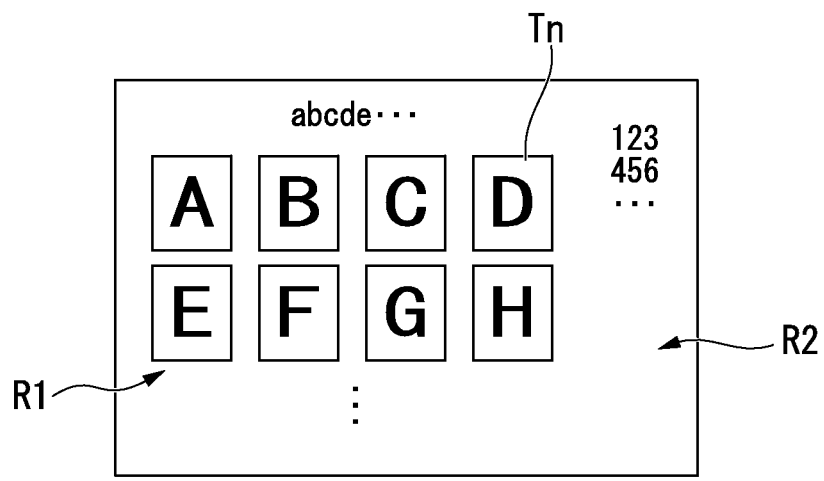
FIG. 10A is a view showing an example of screen display in the standard mode.
Figure 10B:
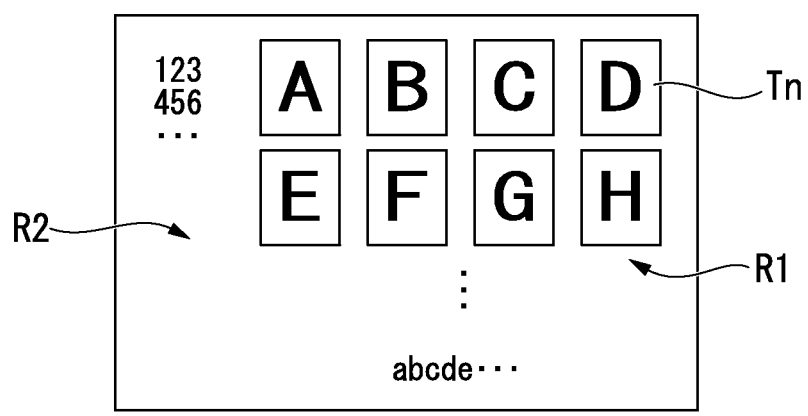
FIG. 10B is a view showing an example of screen display in the inverted mode.

As shown in FIG. 9A, in the standard mode, an image acquired by the imaging mechanism 56 is displayed on the first region R1, and textual information, such as a manipulation menu and various parameters, is displayed on the second region R2. In the inverted mode shown in FIG. 9B, the user views a display on which upper and lower sides are inverted. For this reason, the textual information displayed on the second region R2 is vertically reversed from the state in the standard mode, and is displayed. On the other hand, the upper and lower sides of an image displayed on the first region R1 are not reversed even in the inverted mode. This is provided to keep a correspondence relationship between an image and the manipulation of the first joystick 21. Additionally, when recording is performed by manipulating the freezing/recording button 71A, there is a purpose storing images in the storage unit 53 with a vertically-structured relationship being unified even if the images are recorded in any of the standard mode and the inverted mode.

On the other hand, as for a thumbnail screen showing the list of images stored in the storage unit 53, it is not necessary to take the above-described matter into consideration. Therefore, in the inverted mode shown in FIG. 10B, the images are vertically reversed, and are aligned and displayed within the first region R1. As a result, the orientation of a thumbnail image Tn that the user views is the same as that of the standard mode shown in FIG. 10A. Additionally, as for a retrieve screen (not shown) that displays one image corresponding to an arbitrary thumbnail image Tn selected from the thumbnail screen, an image is vertically reversed and displayed in the inverted mode.

As described above, according to the endoscope apparatus 1 of the present embodiment, the first joystick 21 in a neutral state and the insertion part 10 connected to the housing part 60 are arranged so as to be coaxial with each other. Thus, in the mechanical curving mechanism 23 using the manipulating member 14, the amount of advance or retreat of each manipulating member 14 during curving manipulation becomes uniform, and the curving portion 13 can be suitably curved.

In the lower portion 65 of the housing 61 in which the curving mechanism 23 is accommodated, the first slope 71 is formed above the insertion part 10 and the second slope 72 is formed below the insertion part 10 at the back face 65B to which the insertion part 10 is connected. Thereby, the back face 65B is formed in a convex shape that rises up toward the insertion part 10 in a side view of the housing 61. Accordingly, the hand of the user holding the lower portion 65 is brought into a state where the palm of the hand is made concave so as to wrap around the back face 65B. In addition, at least one finger among the four fingers other than the thumb is arranged on the first slope 71 and the second slope 72 so as to pinch the insertion part 10 in the vertical direction.

As a result, a force, such as a moment that acts on the housing part 60 through the long insertion part 10, can be suitably received by a user's hand regardless of the direction in which the moment acts, and the housing 61 can be stably held.

Moreover, since the position of the center of gravity of the endoscope apparatus 1 excluding the insertion part 10 is set in the above-described region A1. Therefore the user can suitably hold the housing part 60 with the hand holding the lower portion 65, and can suitably stabilize the positions of the upper front face 64A and the lower front face 65A. That is, it is not easily brought about a state which difficult to recognize the display part 40 or to manipulate the manipulating part 20 such as the manipulating part 20 of the upper front face 64A is pushed toward the back face or the lower front face 65A becomes parallel to the perpendicular direction. As a result, manipulation can be performed with the housing part 60 being held in a state where the display 41 is easily seen and the manipulating part 20 is easily manipulated.

Moreover, due to the shape of the lower back face 65B described above, a swinging center 21A of the first joystick 21 is located in a region A2 specified by the first slope 71 and the second slope 72 where user's fingers are arranged when the housing 61 is held and by the distal end 21B of the first joystick 21 that protrudes to the front face 65A, in a side view of the housing 61 shown in FIG. 6. Accordingly, a situation where the housing part 60 is collapsed due to the force that acts on the housing part 60 when the first joystick 21 is manipulated can be suitably suppressed, and an endoscope apparatus that does not easily cause fatigue even if being manipulated for a long period of time can be provided.

Moreover, since the second slope 72 has the first holding face 72A and the second holding face 72B, the tips of fingers (for example, the third finger F3 and the little finger F4) arranged on the second slope 72 are arranged along either the first holding face 72A or the second holding face 72B when the lower portion 65 is held.

Figure 11:
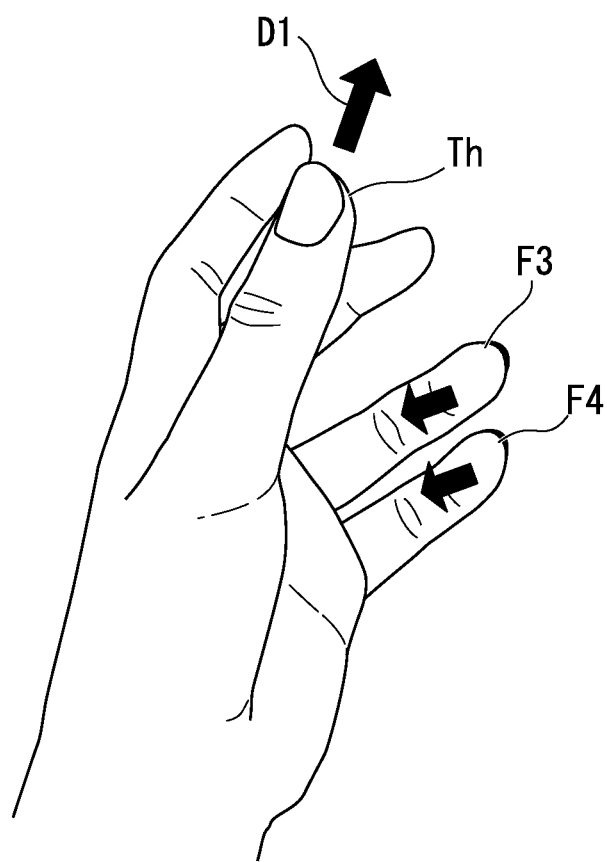
FIG. 11 is a view showing an example of a user's hand holding the housing of the endoscope apparatus.

For this reason, as shown in FIG. 11, the fingers F3 and F4, and the like that are arranged on the second slope 72, and the thumb Th have the positional relationship of substantially facing each other. As a result, when the first joystick 21 is inclined with the thumb Th in the direction (for example, the direction of an arrow D1 shown in FIG. 11) separating from the grip side of the hand, such as the direction in which the thumb Th extends, the force that acts with inclination manipulation by the third finger F3, the little finger F4, and the like to incline the housing 61 can be suitably received, and to perform manipulation while maintaining a state where the housing 61 is stabilized. This effect is similarly exhibited even in an electrical motor-driven type in which the curving mechanism uses a motor or the like. However, since the force that is generated with the manipulation of the first joystick 21 becomes large in a case where a mechanical curving mechanism only using a manipulating member is provided, the effect is greater in the endoscope apparatus like the present embodiment.

This effect is similarly obtained even when a button or the like is arranged on the front to which the thumb Th extends and the button is manipulated in the manipulating part 20. An example in a case where holding and manipulation are performed with the left hand is shown in FIG. 11. In this case, the tip of a finger arranged on the second slope 72 is arranged at the second holding face 72B. When a user performs holding and manipulation with the right hand, the tip of a finger is arranged at the first holding face 72A, but the same effect is exhibited.

Moreover, since the friction members 73 having elasticity are attached to the first holding face 72A and the second holding face 72B. Through this configuration, even when a relatively larger force acts on the finger arranged on the second slope 72, the positional relationship between the second slope 72 and the finger is suitably held. As a result, the housing part 60 can be held even during manipulation, and stable manipulation can be performed.

The second joystick 22 protrudes from the bottom of the concave portion 70 provided in lower of a front face 65A, and the height thereof is set so that the distal end of the second joystick 22 does not protrude from the front face 65A. For this reason, the second joystick 22 is not hindering the manipulation of the first joystick 21, although the second joystick 22 is arranged in a place where the joystick is easily manipulated by the thumb Th around the first joystick 21 and then, operability can be further improved.

In addition, the housing can be suitably self-supported such that the upper portion 64 is turned down and the lower portion 65 is turned up, and can be used in the inverted mode by bringing the housing 61 contact with the ground at the two ground contact members 68 provided at the upper portion 65, and the connecting portion between the insertion part 10 and the housing part. For this reason, the housing can be suitably used even in the manipulation for a prolonged time. Furthermore, through the control of the display control unit 41 described above, showing of the display 41 is easily seen even when being used in the inverted mode, and can be suitably used.

Although one embodiment of the present invention has been described hitherto, the technical scope of the invention is not limited to the above respective embodiments, but various modified examples can be made to respective constituent elements or omissions thereof can be made, without departing from the scope of the invention.

Figure 12:
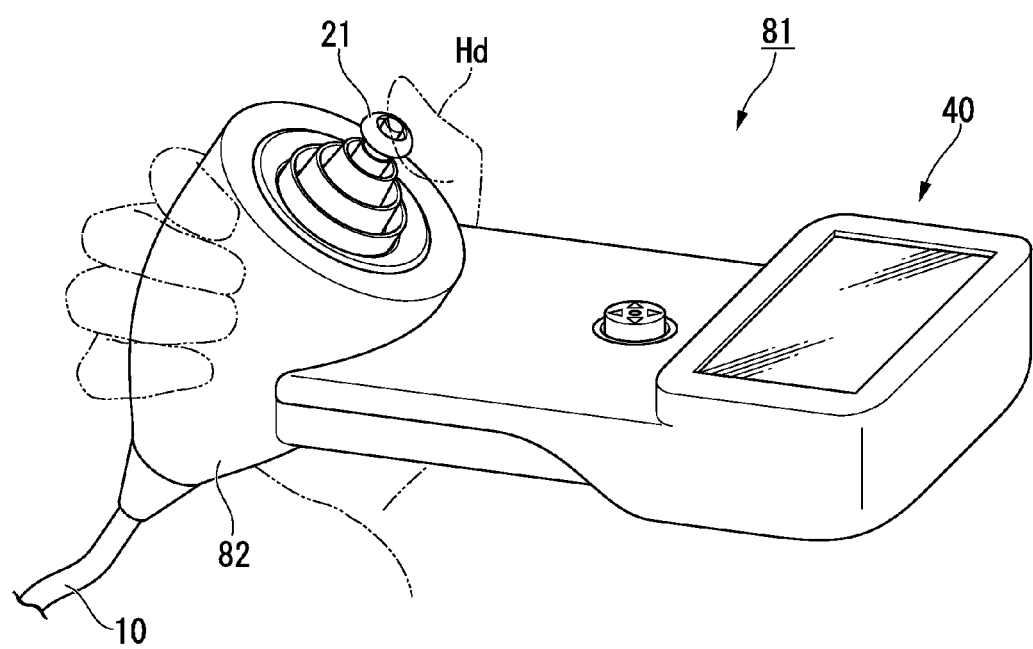
FIG. 12 is an overall perspective view showing an endoscope apparatus of a modified example of the invention.

First, the shape of the grip face in one embodiment of the present invention is not limited to the shape having the first slope and the second slope as described above, and any arbitrary shapes that are convex toward the back face may be adopted. In an endoscope apparatus 81 of a modified example shown in FIG. 12, the grip face 82 is formed in the shape of a spindle that is convex toward the back face. Since such a grip face 82 also fit the curve of a finger of a holding user, the finger can be suitably arranged, and stable holding can be performed. In addition, although a hand Hd is shown by a two-dot chain line in FIG. 12 in a state where the first joystick 21 is placed at the tip side and the display part 40 is placed at the grip side, it is also possible to turn the display part 40 up and hold the display part similarly to the above-described endoscope apparatus 1.

Figure 13:
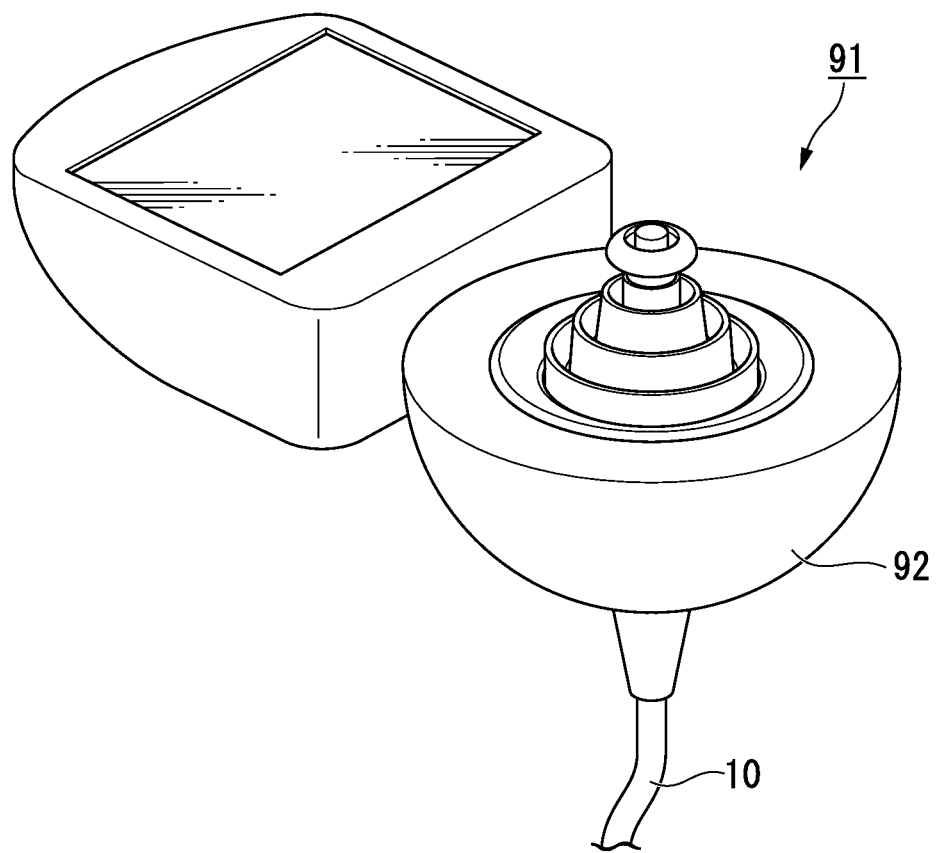
FIG. 13 is an overall perspective view showing an endoscope apparatus of a modified example of the invention.
Figure 14A:
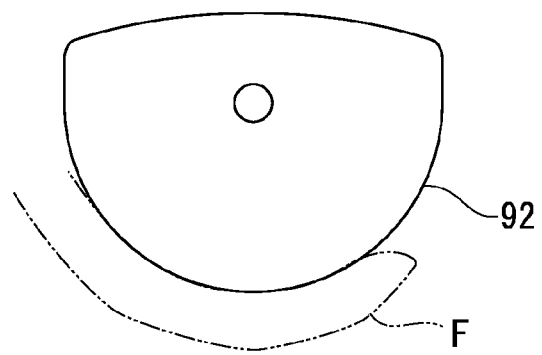
FIG. 14A is a schematic view showing the shape of a grip face in the modified example.

FIG. 13 shows an endoscope apparatus 91 of a modified example of the present invention in which a grip face 92 is formed in the shape of a spherical surface. Since such a grip face 92 also fit the curve of a finger F of a holding user as schematically shown in FIG. 14A, the finger F can be suitably arranged.

FIG. 14B to FIG. 14E schematically show examples of the shape of the grip face, respectively, in bottom views (the same state as FIG. 5) of the housing.

Figure 14B:
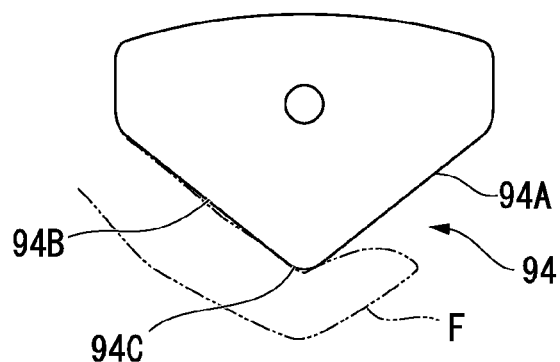
FIG. 14B is a schematic view showing the shape of a grip face in the endoscope apparatus of the modified example of the invention.
Figure 14C:
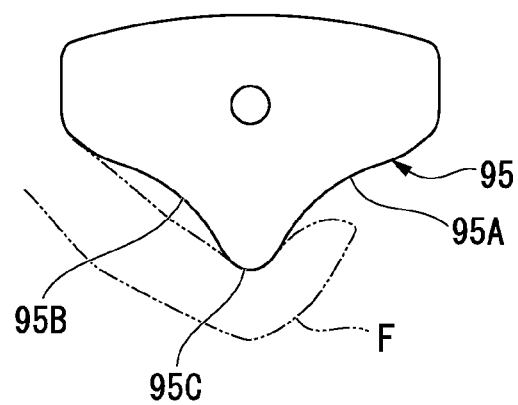
FIG. 14C is a schematic view showing the shape of a grip face in the endoscope apparatus of the modified example of the invention.

A grip face 94 shown in FIG. 14B or a grip face 95 shown in FIG. 14C have a first holding face 94A or 95A and a second holding face 94B or 95B that rise up from the edges of a housing in the right-and-left direction, respectively, and becomes convex toward the back face in the bottom view of the housing. A connecting portion between the first holding face and the second holding face becomes a top portion 94C or 95C. In such a grip face 94 or 95, a user can hook a portion of the finger F (for example, a first joint) on the top portion 94C or 95C, and can further stabilize holding. In the grip face 95, the first holding face 95A and the second holding face 95B are curved with predetermined curvature so as to become concave toward the back face. However, since the grip face has a top portion 95C, the fundamental shape of the grip face 95 is convex toward the back face.

Figure 14D:
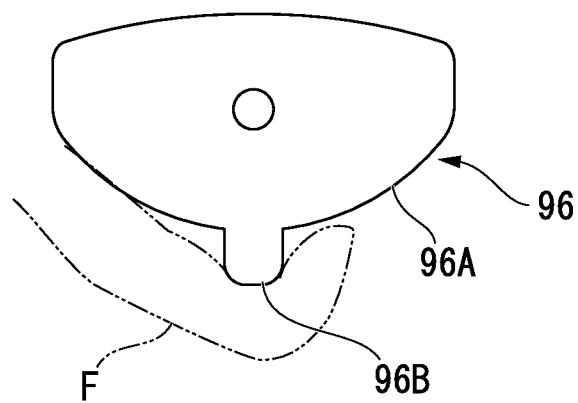
FIG. 14D is a schematic view showing the shape of a grip face in the endoscope apparatus of the modified example of the invention.

A grip face 96 having a convex portion 96B that protrudes above a spherical fundamental face 96A is shown in FIG. 14D. In such a grip face, a user also can hook a first joint of the finger F on the convex portion 96B, and can stabilize holding.

Figure 14E:
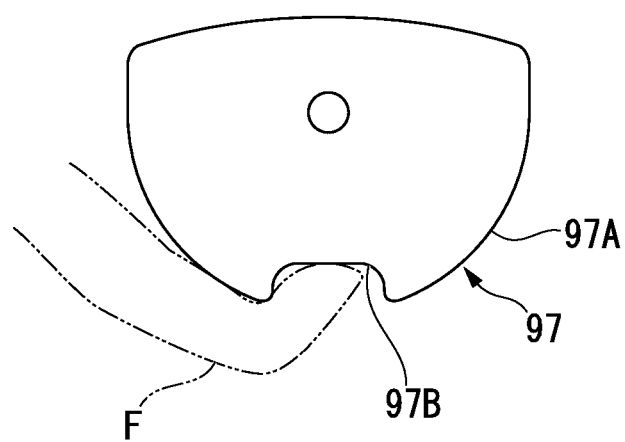
FIG. 14E is a schematic view showing the shape of a grip face in the endoscope apparatus of the modified example of the invention.

A grip face 97 having a concave portion 97B on a spherical fundamental face 97A is shown in FIG. 14E. In such a grip face, a user can hook a first joint of the finger F on the concave portion 97B to stabilize holding. Although the concave portion 97B is not convex toward the back face in the grip face 97, since the grip face has the spherical fundamental face 97A, the fundamental shape is convex toward the back face.

As such, the grip face can be suitably set according to the application of an endoscope apparatus, a target user, or the like while having a fundamental shape that is convex toward the back face. In addition, it is sufficient if the grip face is convex toward the back face in at least one of a side view or a bottom view of the housing. Even if the grip face is not convex toward the back face in both of the side view and bottom view as in the endoscope apparatus 1, the effect that the holding by a user is stabilized to a certain degree is exhibited.

In the above-described embodiments, the example in which the position of the center of gravity of the endoscope apparatus excluding the insertion part is set within the region A1 of the connecting portion between the upper portion and the lower portion of the housing and its surroundings has been described. However, even if the center of gravity is out of the region A1, or even if the center of gravity is set so as to be arranged within the region A3 shown in FIG. 6, the effect that holding and manipulation are stabilized can be obtained to a certain degree.

Furthermore, in the above-described embodiments, the example in which the ground contact members 68 for self-supporting the housing 61 in the inverted mode are arranged at two locations apart from each other has been described. Instead of this, however, the ground contact members may be arranged on one straight line by a predetermined length (for example, to such a degree that two locations where the ground contact members 68 of the present embodiment are arranged are connected together) at an upper peripheral edge portion of the upper back face 64B. Even in this way, the housing 61 can be suitably self-supported and can be used in the inverted mode.

Moreover, in the above-described embodiments, the example in which the illumination mechanism 12 is arranged at the distal end of the insertion part 10 has been described. Instead of this, however, as in the related-art endoscope apparatus, the light source may be arranged within the housing, and the light guide member, such as a light guide, may be arranged within the insertion part to supply illumination light to the distal end of the insertion part.

Furthermore, although the present invention is suitably applied to an endoscope apparatus in which only a battery can be used as a power source, a configuration in which electric power can be supplied from an external power source in addition to the battery may be adopted. At this time, for example, the position of the center of gravity of the endoscope apparatus excluding the insertion part may change greatly due to no mounting of a battery. In this case, an endoscope apparatus may be provided with a dummy member, which has the same shape and size as a battery, is lighter in weight than the battery, and which is capable of setting the position of the center of gravity within a predetermined region in a state where the dummy member is mounted on a battery accommodating portion, and the dummy member may be mounted on the battery accommodating portion and an endoscope apparatus may be used when an external power source is used.

Furthermore, in the above-described embodiments, the example in which the friction members having elasticity are attached to the first holding face and the second holding face has been described. And so forth, even if a member that does not deform elastically is selected as the friction member, and this member is attached to each holding face so as to enhance only the frictional coefficient, a certain effect can be exhibited.

Moreover, in the above-described embodiments, the example in which the reinforce member and the self-supporting auxiliary member are attached to the proximal end portion of the insertion part connected to the housing has been described. In addition, only one of the reinforcing member and the self-supporting auxiliary member may be attached to the proximal end portion. And so forth, an endoscope apparatus capable of being self-supported only by the connecting portion of the insertion part, and the edge of the housing at the display part without being attached to any of the reinforcing member and the self-supporting auxiliary member may be configured.

Although, the preferred examples of the present invention have been described hitherto, the technical scope of the invention is not limited to the above respective examples. Additions, omissions, substitutions, and other modifications can be made, without departing from the scope of the invention. In addition, the present invention is not limited by the above description and is limited only by the scope of the appended claims.

The invention claimed is:
1. An endoscope apparatus comprising:
an insertion part which has an imaging mechanism at a distal end portion and which is bendable and elongated;
a display part which displays an image acquired by the imaging mechanism;
a manipulating part which performs curving manipulation of the insertion part; and a housing provided with the display part and the manipulating part at a front face thereof, and connected to the insertion part at a back face opposite to the front face, wherein the manipulating part comprises:
  a swingable manipulating rod, and
  a curving mechanism that has the manipulating rod and a manipulating member connected thereto and that curves the insertion part as the manipulating member is advanced or retracted by manipulating the manipulating rod, wherein the housing has an upper portion where the display part is provided, and a lower portion where the manipulating part is provided and to which the insertion part is connected, wherein a proximal end of the insertion part connected to the lower portion, and the manipulating rod are coaxially arranged in a neutral state of the manipulating rod, wherein the back face of the lower portion includes a first finger grip portion having a first slope and a second finger grip portion having a second slope, wherein the insertion part is connected to the lower portion between the first finger grip portion and the second finger grip portion, wherein the first finger grip portion, which is provided above the proximal end of the insertion part, includes a first finger grip and a second finger grip, wherein the second finger grip is provided between the first finger grip and the proximal end of the insertion part, such that the second finger grip is provided below the first finger grip in a vertical direction, and the proximal end of the insertion part is provided below the second finger grip in the vertical direction, wherein the housing is configured to be held by a single hand of a user, such that (i) a thumb of the single hand of the user is located at a distal end of the manipulating rod, (ii) first and second other fingers in the single hand of the user are located respectively on the first finger grip and the second finger grip of the first finger grip portion, (iii) third and fourth other fingers in the single hand of the user are located on the second finger grip portion, and (iv) the thumb and the other fingers face each other, and wherein a swinging center of the manipulating rod is located inside a region specified by the first slope of the first finger grip portion and the second slope of the second finger grip portion, and by the distal end of the manipulating rod protruding from the front face in a side view of the housing.

2. The endoscope apparatus according to claim 1, wherein the first slope and the second slope both incline toward the insertion part.

3. The endoscope apparatus according to claim 2, wherein the curving mechanism is a mechanical curving mechanism in which the manipulating member is advanced or retracted by manipulating the manipulating rod.

4. The endoscope apparatus according to claim 2, wherein the first slope extends downward and rearward toward the proximal end of the insertion part, and the second slope extends upward and rearward toward the proximal end of the insertion part.

5. The endoscope apparatus according to claim 1, wherein the curving mechanism is a mechanical curving mechanism in which the manipulating member is advanced or retracted by manipulating the manipulating rod.

6. The endoscope apparatus according to claim 1, wherein the first finger grip portion comprises:
  a first extending section that extends rearward and downward toward the proximal end of the insertion part from a position of the back face of the housing where the upper portion of the housing meets the lower portion of the housing;
  a second extending section that extends rearward and downward toward the proximal end of the insertion part from a distal end of the first extending section; and
  wherein the first finger grip is provided at the first extending section, and the second finger grip is provided at the second extending section.

7. The endoscope apparatus according to claim 6, wherein the second extending section is curved.

8. The endoscope apparatus according to claim 6, wherein the first extending section is linear and provides an upwardly facing surface; and
  wherein the second extending section is curved.

* * * * *